United States Patent [19]

Drought

[11] Patent Number: 5,678,538
[45] Date of Patent: Oct. 21, 1997

[54] INHALATION DEVICE

[75] Inventor: Nicholas A. M. Drought, Cambridge, United Kingdom

[73] Assignee: Fisons PLC, United Kingdom

[21] Appl. No.: 530,214

[22] PCT Filed: Mar. 31, 1994

[86] PCT No.: PCT/GB94/00712

§ 371 Date: Jan. 2, 1996

§ 102(e) Date: Jan. 2, 1996

[87] PCT Pub. No.: WO94/22515

PCT Pub. Date: Oct. 13, 1994

[51] Int. Cl.[6] .................................................. A61M 15/00
[52] U.S. Cl. .................. 128/203.15; 128/203.21
[58] Field of Search ................. 128/203.15, 203.21; 604/58

[56] References Cited

U.S. PATENT DOCUMENTS

| 1,934,793 | 11/1933 | Crain et al. | 604/58 |
|---|---|---|---|
| 4,524,769 | 6/1985 | Wetterlin | 128/203.15 |
| 4,667,668 | 5/1987 | Wetterlin | 128/203.15 |
| 4,841,964 | 6/1989 | Hurka et al. | 128/203.15 |
| 4,907,583 | 3/1990 | Wetterlin | 128/203.15 |
| 5,176,132 | 1/1993 | Drought et al. | 128/203.21 |
| 5,341,800 | 8/1994 | Clark et al. | 128/203.21 |
| 5,469,843 | 11/1995 | Hodson | 604/58 |

*Primary Examiner*—Aaron J. Lewis
*Attorney, Agent, or Firm*—Nixon, Hargrave, Devans & Doyle

[57] ABSTRACT

A medication inhalation device includes a housing having a through-going pathway connecting an air inlet with an air outlet, a medicament reservoir adapted to receive a compacted body of powdered medicament, and metering means for dispensing a predetermined dose of medicament from the reservoir into the through-going pathway, the metering means including means for abrading the compacted body; the device is provided with a shutter movable between a first position in which the compacted body is isolated from the through-going pathway and a second position in which the compacted body is in communication with the through-going pathway wuch that a dose of medicament can be dispensed from the reservoir into the through-going pathway.

10 Claims, 3 Drawing Sheets

INHALATION DEVICE

This invention relates to a device for the administration of powdered medicaments by inhalation, more particularly to a multiple-dose inhalation device with metering means for dispensing pre-determined doses from a medicament reservoir.

European Patent Application 407028 (Fisons plc) discloses a multiple-dose inhalation device in which a dose of medicament is metered by abrading a fixed volume from a compacted body of powdered medicament. The metered dose is then entrained in a through-going pathway of the device and is inhaled by the patient, the means for abrading being, for example, a helical blade. Other devices which use the principle of abrading a compacted body of powdered medicament are disclosed in International Patent Applications WO 92/04067 (Boehringer Ingelheim KG) and WO 93/24165 (GGU Gesellschaft für Gesundheits- und Umweltforschung mbH & Co. Vertriebs KG).

Such devices may offer improved dose consistency when compared to multiple-dose devices which rely on gravitational force to meter a dose of medicament from a reservoir. However, inaccuracies in dosing may still occur due to incomplete removal of the abraded dose from the compacted body, or by the removal of additional quantities of powder from the body during inhalation by the patient. Furthermore, if such devices are inadvertently dropped quantities of medicament could break off from the compacted body and enter the through-going pathway of the device, resulting in a multiple dose being administered when the patient next uses the device.

We have now found that these disadvantages can be overcome or substantially mitigated by providing a shuttering system in the device which is capable of isolating the compacted body of medicament from the through-going pathway of the device.

Thus, according to the invention, there is provided a medicament inhalation device including a housing having a through-going pathway connecting an air inlet with an air outlet, a medicament reservoir adapted to receive a compacted body of powdered medicament, and metering means for dispensing a predetermined dose of medicament from the reservoir into the through-going pathway, the metering means including means for abrading the compacted body; characterised in that the device is provided with a shutter movable between a first position in which the compacted body is isolated from the through-going pathway and a second position in which the compacted body is in communication with the through-going pathway such that a dose of medicament can be dispensed from the reservoir into the through-going pathway.

The means for abrading the compacted body preferably includes a blade which cuts, planes, scrapes or otherwise erodes a surface of the compacted body by relative rotation or sliding between them. For example, the blade may have a helical shape, in which case the dose abraded from the compacted body of medicament will depend inter alia upon the pitch of the helix, the diameter of the blade, the density of the compacted body, and the angle through which the blade is rotated. Alternatively, the means for abrading the compacted body may include a brush or other abrasive surface.

The shutter is preferably biassed into the first position in which the compacted body is isolated from the through-going pathway.

The shutter may be mounted on a carrier, the carrier being adapted to move within the housing of the device, e.g. in an axial direction. Movement of the shutter between the first and second positions may then be effected by the action of a cam on the carrier. The carrier is preferably kept in contact with the cam surface by biassing means, e.g. a cantilever, provided on the carrier which bears against a stationary part of the device. The cam is preferably arranged such that the shutter moves from the first position to the second position prior to the metering of a predetermined dose of medicament from the reservoir, and returns to the first position once the predetermined dose of medicament has been metered. In addition, the shutter preferably returns to the first position before the patient inhales the dose of medicament from the device.

When the shutter returns to the first position before the patient inhales the dose of medicament from the device, the shutter is preferably adapted to sever the metered dose of medicament from the reservoir upon moving from the second position to the first position. The dose of medicament is then deposited in a holding chamber located in the through-going pathway, where it stays until the patient inhales from the device. When the shutter is adapted to sever the metered dose of medicament from the reservoir it preferably comprises a metal blade.

The through-going pathway of the device may also include a dispersion chamber located between the holding chamber and the mouthpiece. The dispersion chamber may be provided with tangential air inlets which serve to provide a swirling flow of air in the chamber thus assisting the dispersion of the medicament.

The shutter movement and metering operations may be controlled by a drive mechanism located within the device.

The drive mechanism is preferably associated with a drive sleeve rotatably mounted on the housing of the device. Rotation of the drive sleeve causes rotation of a cam which is translated into the axial movement of the carrier and shutter, and also the relative movement of the metering means and the compacted body of medicament required for abrasion of the compacted body. In this manner the shutter movement and metering operations may be performed sequentially in response to a single action by the patient. The degree of rotation and hence the amount of medicament abraded is preferably controlled by rotation control means, for example a ratchet associated with the drive means and/or stops provided on the housing, which will only permit rotation through a predetermined angle for each dose.

The shutter carrier can conveniently be configured such that it largely separates the drive mechanism for the device from the through-going pathway. This has the advantage that it reduces the risk of ingress of medicament into the drive mechanism.

Compacted bodies of powdered medicament include bodies of medicament produced by compressing a sample of loose powder so that the medicament particles hold together. The degree of compaction obtained will clearly depend upon the compression force applied to the sample of loose powder, as described in European Patent Application 407028 (Fisons plc), the disclosure of which is hereby incorporated by reference. However, in general, the degree of compaction will be sufficient to impart said compacted body with structural integrity such that a plurality of unit doses of medicament can metered therefrom by abrasion.

The compacted body of inhalation medicament may have any convenient external shape, for example cylindrical or brick-like. However, we prefer the compacted body to have an annular configuration. Annular compacted bodies of medicament may be made by the method described in International Patent Application WO 94/00291 (Fisons plc), the disclosure of which is hereby incorporated by reference.

Medicaments which may be administered from the device according to the invention may include any active ingredients which are conventionally administered by inhalation in powdered form. Such active ingredients include drugs for use in the prophylactic or remedial treatment of reversible obstructive airways disease. Specific active ingredients which may be mentioned include salts of cromoglycic acid, e.g. sodium cromoglycate; salts of nedocromil, e.g. nedocromil sodium; inhaled steroids such as beclomethasone dipropionate, tipredane, budesonide and fluticasone; anticholinergic agents such as ipratropium bromide; bronchodilators, e.g. salmeterol, salbutamol, reproterol, terbutaline, isoprenaline and fenoterol, and salts thereof. If desired a mixture of active ingredients, for example, a mixture of sodium cromoglycate and a bronchodilator, such as salbutamol, reproterol, isoprenaline, terbutaline, fenoterol or a salt of any one thereof, may be used.

The devices according to the present invention may be designed for limited use, i.e. they may be supplied with an integral compacted body of medicament, the device being discarded when this is exhausted; or they may be reusable, i.e. replacement compacted bodies may be provided for insertion into the device.

Thus, according to a further aspect of the invention we provide a device as described above, wherein the medicament reservoir contains a compacted body of powdered medicament.

The devices of the present invention overcome the disadvantages of prior art devices in that the dosing consistency is improved because the shutter severs the dose cleanly at the end of the dose abrasion operation; they prevent the patient back-breathing onto the compacted body of medicament thereby providing improved moisture protection for the medicament; they are easier to use. Furthermore, since the shutter isolates the compacted body of medicament from the through-going pathway during inhalation, it prevents the patient inadvertently inhaling additional drug out of the reservoir.

Although the invention has been described for use in oral inhalation of medicaments, it is also suitable for the administration of nasal medicaments by inhalation. The necessary adaptation for this mode of administration will be readily apparent to those skilled in the art.

A preferred embodiment of the present invention will now be described, by way of example, with reference to the following drawings, in which.

Figure 1:
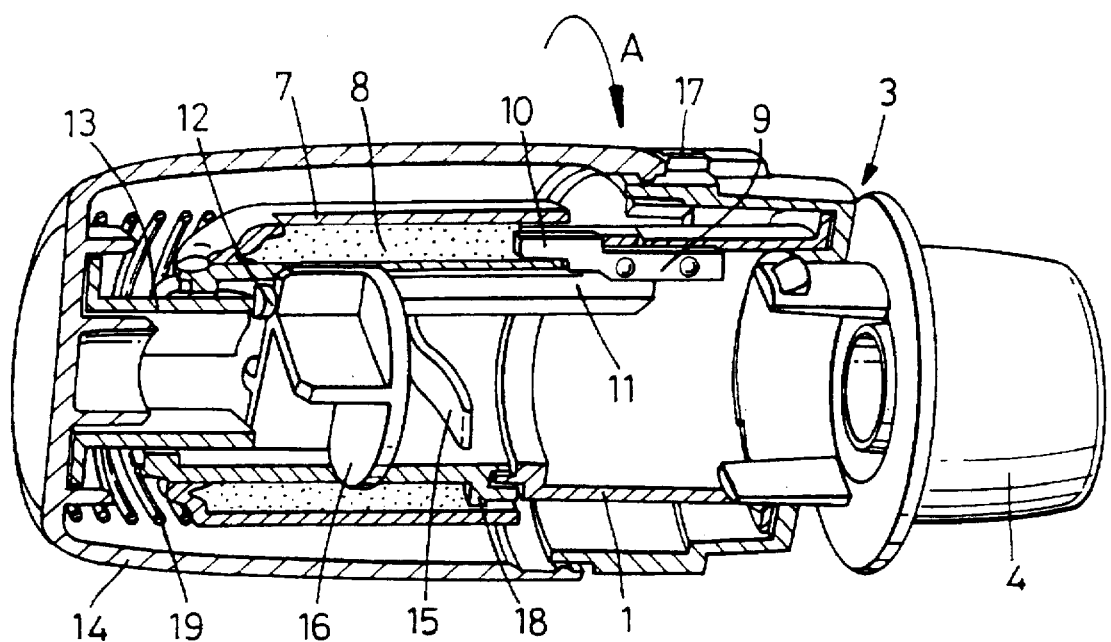
FIG. 1 is a longitudinal view in partial section of a device according to the present invention in the first/rest position (dispersion chamber not illustrated)

A device according to the invention includes a housing (1) having a through-going pathway (2) connecting an air inlet (3) with an air outlet in the form of mouthpiece (4) having a mouthpiece cover (not shown). A dispersion chamber (5) having tangential air inlets (6, 6a) is located in the through-going pathway between air inlet (3) and mouthpiece (4).

A generally cylindrical medicament reservoir (7) containing an annular compacted body of powdered inhalation medicament (8) is rotatably mounted on the housing (1) adjacent to the through-going pathway (2) upstream from the dispersion chamber (5).

Figure 2:
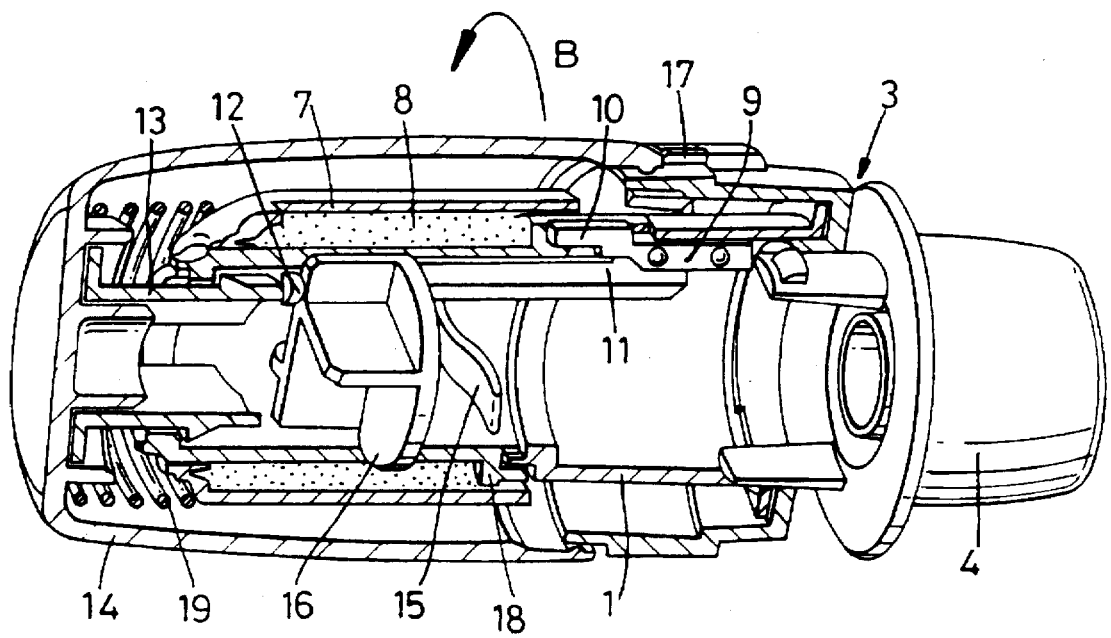
FIG. 2 is a longitudinal view in partial section of the device of FIG. 1 in the second/metering position.
Figure 3:
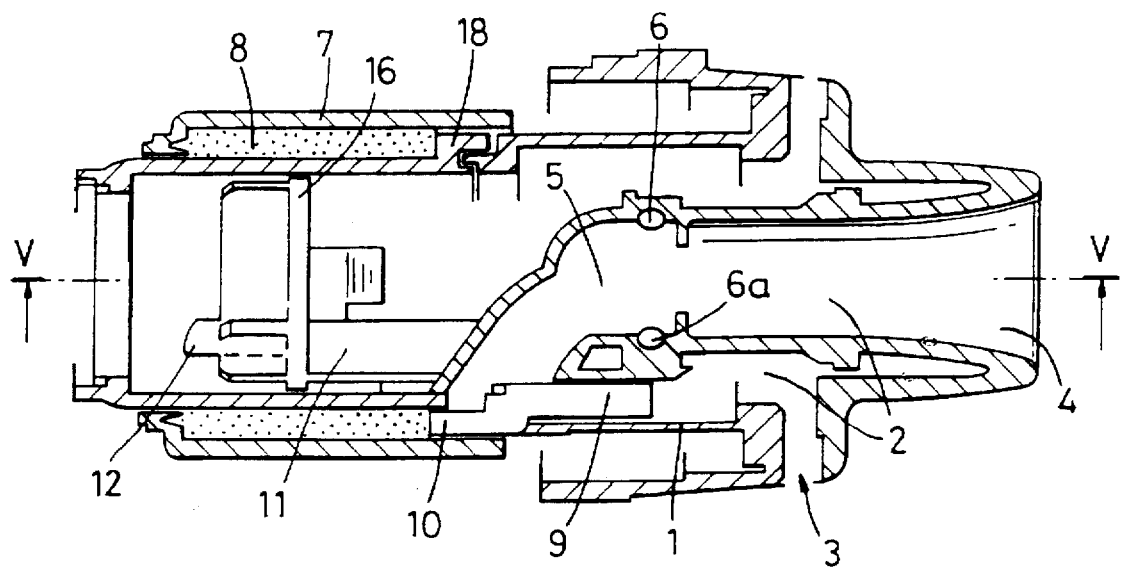
FIG. 3 is a longitudinal section showing in detail the shutter, reservoir and through-going pathway of a device according to the invention in the first/rest position.
Figure 4:
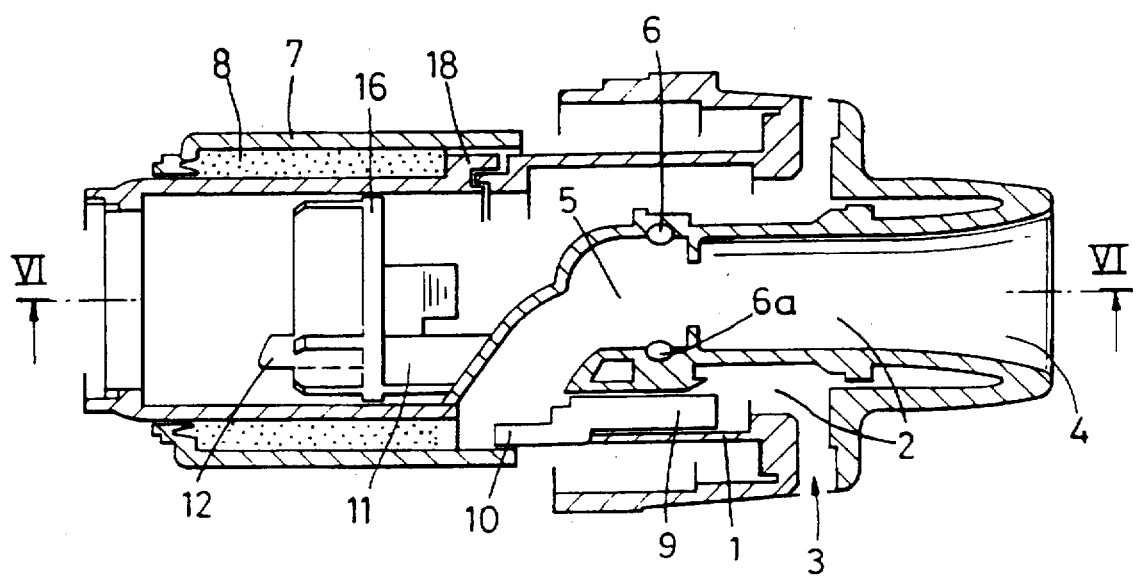
FIG. 4 is a longitudinal section of the device of FIG. 3 in the second/metering position.
Figure 5:
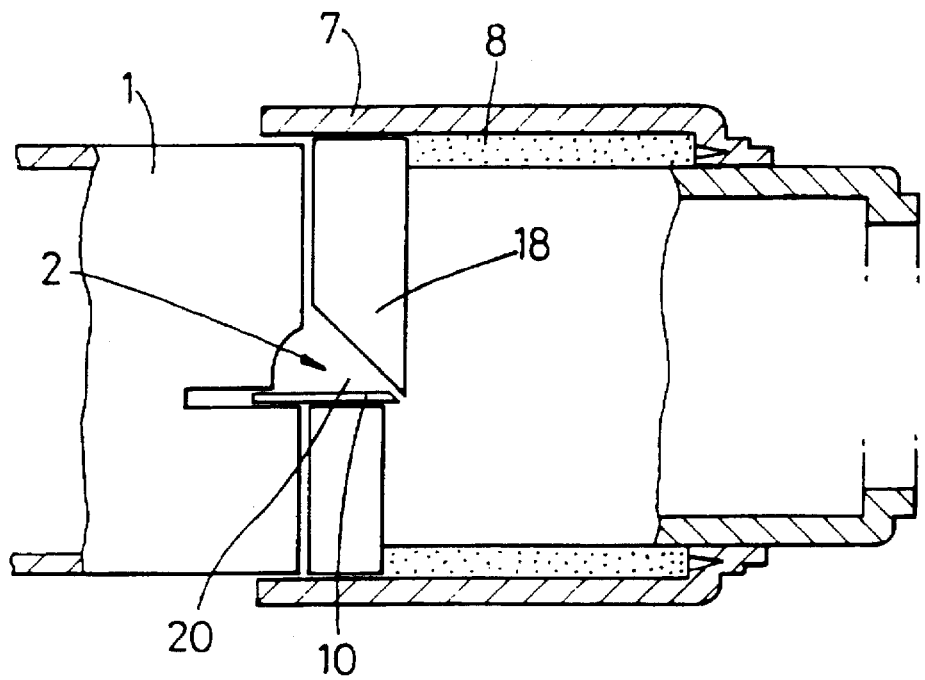
FIG. 5 is a partial section of the shutter and reservoir of the device of FIG. 3 along the line V—V.
Figure 6:
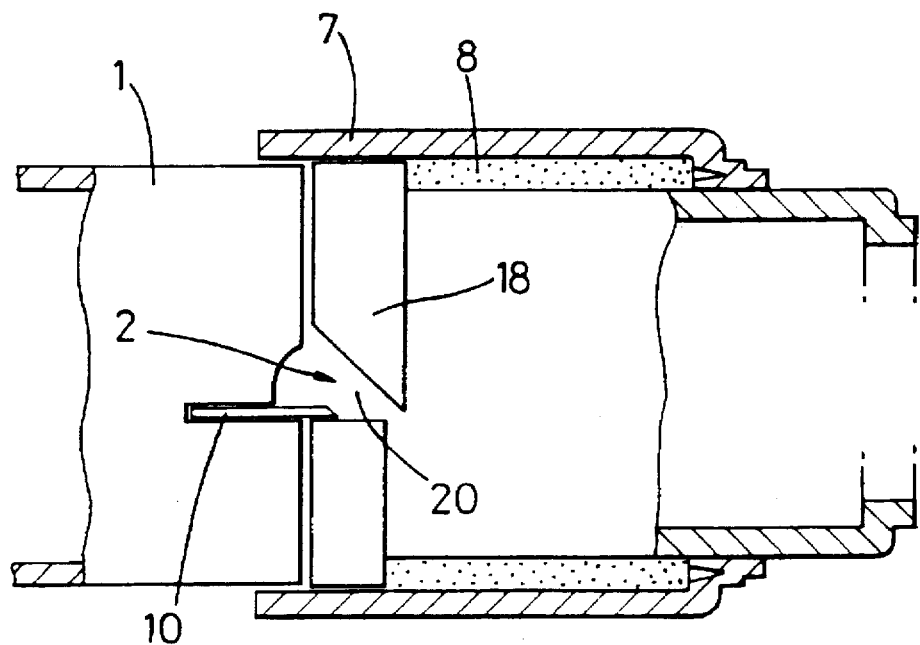
FIG. 6 is a partial section of the shutter and reservoir of the device of FIG. 4 along the line VI—VI.

A shutter (9) comprising a metal blade (10) is mounted on a carrier (11) which is adapted to move axially within the housing between a first/rest position [FIG. 1] in which the compacted body (8) is isolated from the through-going pathway (2), and a second/metering position [FIG. 2] in which the compacted body (8) is in communication with the through-going pathway (2). The end of carrier (11) remote from the shutter (9) is provided with a lug (12) adapted to interact with a cam (13) provided on the inside of a drive sleeve (14) rotatably mounted on the housing (1). The carrier (11) is biassed against the cam (13) by a half cantilever (15) provided on the carrier (11) which bears against an exterior wall of the dispersion chamber (5). The end of the carrier (11) remote from the shutter (9) is also provided with a disc (16) having a diameter generally corresponding to that of the interior of the housing (1). Disc (16) thus separates the cam (13) and reservoir drive mechanism (described below) from the through-going pathway (2) thus reducing the risk of ingress of medicament into the drive mechanism.

Drive sleeve (14) is also provided with a reservoir drive mechanism (not shown) which is adapted to rotate the medicament reservoir (7) through a predetermined angle relative to the housing (1), the angle of rotation being limited by a stop (17) provided on the exterior of the housing.

A helical blade (18) is fixedly mounted in the housing between the reservoir (7) and the mouthpiece (4), such that the blade (18) abuts against the face of the body of compacted medicament (8) contained in the reservoir (7). The body of compacted medicament (8) is further urged towards blade (18) by a compression spring (19) which acts against the outer wall of medicament reservoir (7) and the interior of drive sleeve (14).

In use, drive sleeve (14) is rotated in the direction of arrow A in FIG. 1. The initial part of the rotation causes the cam (13) to move carrier (11) axially within the housing (1) towards mouthpiece (4). The shutter (9) thus moves from the first/rest position [FIG. 1] to the second/metering position [FIG. 2]. Once the compacted body (8) is in communication with the through-going pathway (2), further rotation operates the reservoir drive means (not shown) thus advancing the reservoir (7) and compacted body (8) through an angle of 60°, the degree of rotation being limited by stop (17) provided on the outside of the housing (1). As the reservoir (7) rotates helical blade (18) abrades a predetermined quantity of powdered medicament from the face of compacted body (8).

The drive sleeve (14) is then rotated in the direction of arrow B in FIG. 2. Cam surface (13) rotates back to its original position allowing the shutter (9) to return to its first/rest position under the bias of cantilever (15). As the shutter (9) returns to the first/rest position the metal blade (10) severs the abraded dose of medicament from the compacted body (8), the dose being deposited in holding chamber (20) in the through-going pathway (2), the chamber (20) being defined in part by the blade (18) and shutter (9). The patient then removes the mouthpiece cover (not shown) and inhales at the mouthpiece (4) drawing air through air inlet (3) and through-going pathway (2). The dose of medicament drawn into dispersion chamber (5) where it is entrained in the air flow and inhaled by the patient. During inhalation the shutter (9) prevents additional medicament from being scoured from the compacted body (8) since it isolates the compacted body (8) from the through-going pathway (2).

I claim:

1. A medicament inhalation device comprising a housing (1) having a through-going pathway (2) connecting an air inlet (3) with an air outlet (4), a medicament reservoir (7) for receiving a compacted body of powdered medicament (8), and metering means for dispensing a predetermined dose of medicament from the reservoir (7) into the through-going pathway (2), the metering means including means (18) for abrading the compacted body (8) which extends into the reservoir 7; characterized in that the device is provided with a shutter (9) movable between a first position in which the reservoir (7) is isolated from the through-going pathway (2) and a second position in which the reservoir (7) is in communication with the through-going pathway (2) such that a dose of medicament can be dispensed from the reservoir (7) into the through-going pathway (2).

2. A device according to claim 1, wherein the medicament reservoir (7) contains a compacted body of powdered medicament (8).

3. A device according to claim 1, further comprising means for biassing the shutter (9) into the first position in which the reservoir (7) is isolated from the through-going pathway (2).

4. A device according claim 1, wherein the shutter (9) moves from the first position to the second position prior to the metering of a predetermined dose of medicament from the reservoir (7).

5. A device according to claim 4, further comprising means for biassing the shutter (9) to return to the first position.

6. A device according to claim 1, further comprising a carrier (11) on which the shutter (9) is mounted, the carrier (11) arranged to move axially within the housing (1).

7. A device according to claim 1, further comprising a cam (13) which is mounted in the housing to effect movement of the shutter (9).

8. A device according to claim 7 further comprising a carrier (11) on which the shutter (9) is mounted, the carrier (11) arranged to move axially within the housing (1).

9. A device according to claim 1, wherein the shutter (9) is adapted to sever the metered dose of medicament from the reservoir (7) upon moving from the second to the first position.

10. A device according to claim 9, wherein the shutter (9) comprises a metal blade (10).

* * * * *